US012582721B2

(12) United States Patent
Fuior et al.

(10) Patent No.: US 12,582,721 B2
(45) Date of Patent: Mar. 24, 2026

(54) MOLYBDENUM-BASED FEED SUPPLEMENT FOR BEES

(71) Applicants: UNIVERSITE DE VERSAILLES—SAINT-QUENTIN-EN-YVELINES, Versailles (FR); CENTRE NATIONAL DE LA RECHERCHE SCIENTIFIQUE, Paris (FR); INSTITUTUL DE ZOOLOGIE, Chisinau (MD); UNIVERSITATEA DE STAT DIN MOLDOVA, Chisinau (MD)

(72) Inventors: Arcadie Fuior, Versailles (FR); Sébastien Floquet, Versailles (FR); Valentina Cebotari, Chisinau (MD); Diana Cebotari, Versailles (FR); Aurelian Gulea, Chisinau (MD); Ion Toderas, Chisinau (MD)

(73) Assignees: UNIVERSITE DE VERSAILLES QUENTIN-EN-YVELINES, Versailles (FR); CENTRE NATIONAL DE LA RECHERCHE SCIENTIFIQUE, Paris (FR); INSTITUTUL DE ZOOLOGIE, Chisinau (MD); UNIVERSITATEA DE STAT DIN MOLDOVA, Chisinau (MD)

( * ) Notice: Subject to any disclaimer, the term of this patent is extended or adjusted under 35 U.S.C. 154(b) by 459 days.

(21) Appl. No.: 18/006,083

(22) PCT Filed: Jul. 19, 2021

(86) PCT No.: PCT/EP2021/070097
§ 371 (c)(1),
(2) Date: Jan. 19, 2023

(87) PCT Pub. No.: WO2022/018009
PCT Pub. Date: Jan. 27, 2022

(65) Prior Publication Data
US 2023/0346950 A1 Nov. 2, 2023

(30) Foreign Application Priority Data
Jul. 23, 2020 (FR) ...................................... 2007784

(51) Int. Cl.
| | |
|---|---|
| *A61K 47/54* | (2017.01) |
| *A01K 51/00* | (2006.01) |
| *A01K 53/00* | (2006.01) |
| *A23K 20/20* | (2016.01) |
| *A23K 20/22* | (2016.01) |
| *A23K 50/00* | (2016.01) |
| *A61K 47/24* | (2006.01) |
| *A61P 33/14* | (2006.01) |

(52) U.S. Cl.
CPC ............ *A61K 47/547* (2017.08); *A01K 51/00* (2013.01); *A01K 53/00* (2013.01); *A23K 20/22* (2016.05); *A23K 20/30* (2016.05); *A23K 50/00* (2016.05); *A61K 47/24* (2013.01); *A61P 33/14* (2018.01)

(58) Field of Classification Search
CPC ....... A61P 33/14; A61K 47/547; A61K 47/24; A23K 20/22; A23K 20/30; A23K 50/00; A01K 51/00; A01K 53/00
See application file for complete search history.

(56) References Cited

FOREIGN PATENT DOCUMENTS

| | | | |
|---|---|---|---|
| DE | 102005028170 A1 | | 2/2007 |
| JP | 2011116700 | * | 6/2011 |
| JP | 2011116700 A | | 6/2011 |
| MD | 20150005 A2 | * | 4/2016 |

OTHER PUBLICATIONS

Philip L. Gould, Salt Selection for Basic Drugs, 33 Int'l. J Pharmaceut. 201 (Year: 1986).*
Deepak Gupta, et al, Salts of Therapeutic Agents: Chemical, Physicochemical, and Biological Considerations, 23 MOL. 1719 (Year: 2018).*
MD-20150005 Machine Translation (Year: 2016).*
JP2011116700 Machine Translation (Year: 2011).*
Office Action issued on Dec. 11, 2024, in corresponding Chinese Application No. 202180049769.0, 14 pages.
Kloubek et al., "Molybdenum(III) Complexes of Ethylenediaminetetraacetic Acid", J. Inorg. Nucl. Chem., Pergamon Press, Dec. 31, 1970, vol. 33, pp. 2981-2988.
Wu et al., "Two Novel Molybdenum Complexes Containing [Mo2O2S2]2+ Fragment: Synthesis, Crystal Structures and Catalytic Studies", Applied Organometallic Chemistry, Materials, Nanoscience and Catalysis, John Wiley & Sons, Ltd., Oct. 8, 2007, vol. 21, pp. 1033-1040.
Kathirgamanathan et al., "Complete Synthesis of the Series of Triangular Oxo/Sulphido Bridged Molybdenum(IV) Complexes as Aqua Ions", J. Chem. Soc., Chem. Commun., Jan. 1, 1985, pp. 1437-1439.
Luo et al., "Layered Lanthanide Molybdate Pillared by Chiral [λ-Mo2O4EDTA]2-", Inorganic Chemistry, American Chemical Society, Dec. 1, 2006, vol. 45, No. 26, pp. 11030-11034.
International Search Report issued on Sep. 30, 2021 in corresponding International Patent Application No. PCT/EP2021/070097, 6 pages.
Preliminary Search Report issued on Apr. 20, 2021 in corresponding French Patent Application No. 2008136, 18 pages.

(Continued)

*Primary Examiner* — Sean M Basquill
(74) *Attorney, Agent, or Firm* — Maier & Maier, PLLC

(57) ABSTRACT

Food supplements for bees that include molybdenum complexes and a method of administering the food supplements to the bees for preventing the infestation of bees and their larvae by the *Varroa destructor* mite. Also, the use of the food supplements to increase the production of honey and lower the winter mortality of bees.

8 Claims, 2 Drawing Sheets

(56)  References Cited

OTHER PUBLICATIONS

Kast et al, "Distribution of coumaphos in beeswax after treatment of honeybee colonies with CheckMite against the parasitical mite", Dec. 2, 2019 (Dec. 2, 2019), vol. 51, No. 1, pp. 112-122, XP037029092.

Ziegelmann et al, "Lithium chloride effectively kills the honey bee parasite Varroa destructor by a systemic mode of action", Jan. 12, 2018 (Jan. 12, 2018), Scientific Reports.

Anoopkumar-Dukie et al, "Resazurin assay of radiation response in cultured cells", The British Journal of Radiology, 78, Apr. 22, 2005, 945-947.

Zhang et al, "Neutral Red (NR) Assay for Cell Viability and Xenobiotic-Induced Cytotoxicity in Primary Cultures of Human and Rat Hepatocytes", Cell Biology and Toxicology, vol. 6, No. 2, 1990.

Repetto et al, "Neutral red uptake assay for the estimation of cell viability/cytotoxicity", Nature Publishing Group, Published online Jun. 12, 2008.

* cited by examiner

[Fig. 1]
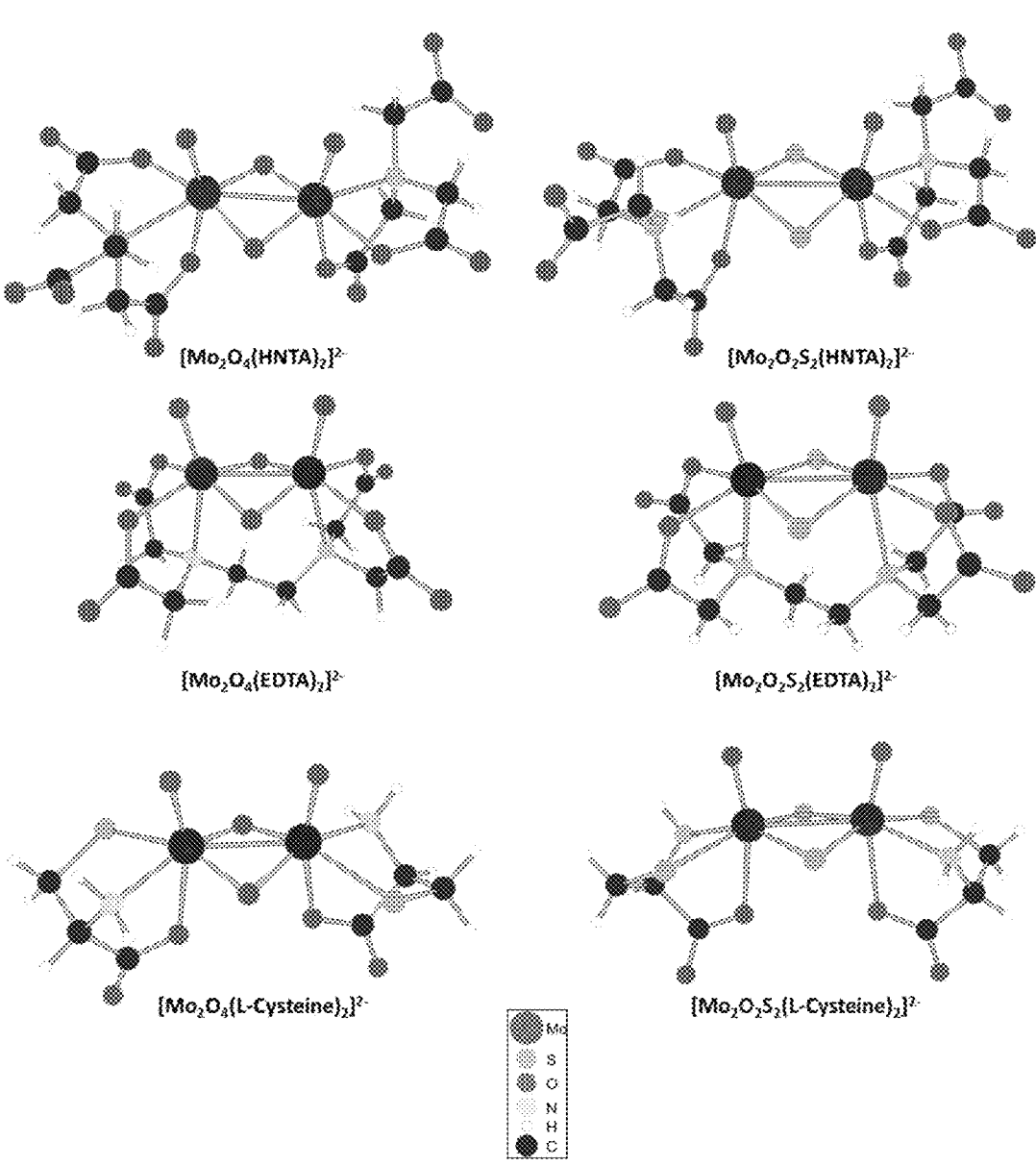

[Fig. 2A]
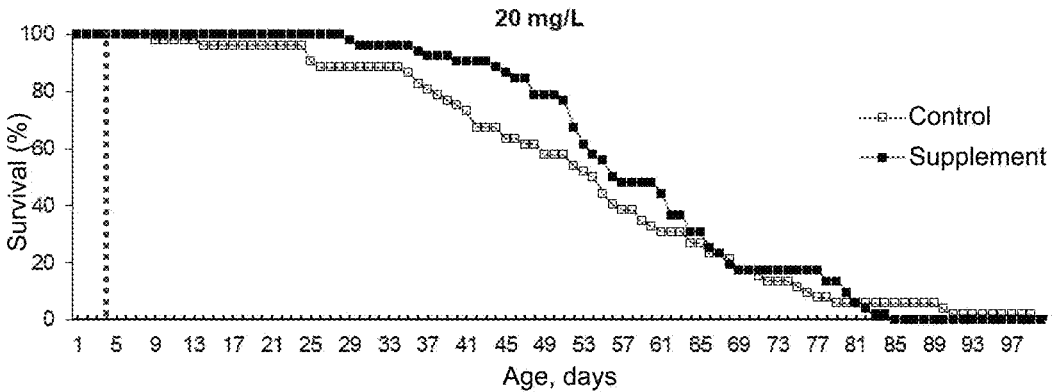
[Fig. 2B]
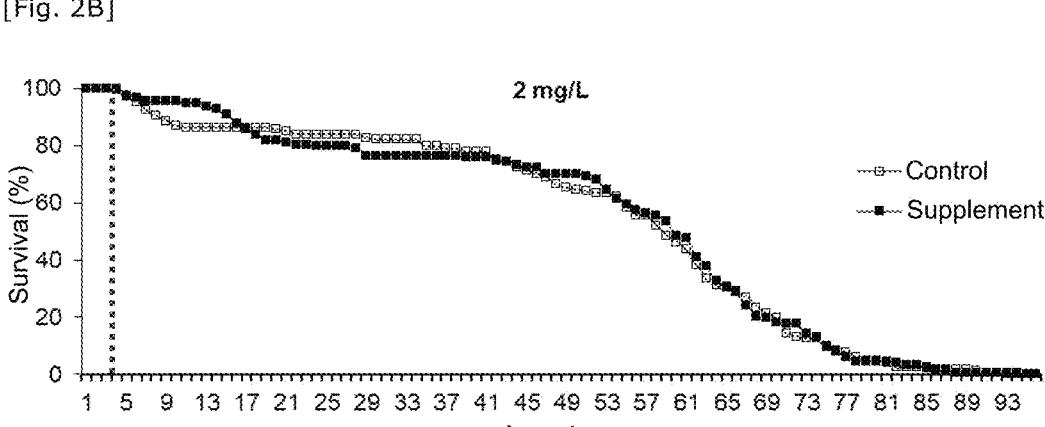

MOLYBDENUM-BASED FEED SUPPLEMENT FOR BEES

FIELD

The present invention relates to food supplements for bees comprising molybdenum complexes and a method for preventing the infestation of bees and their larvae by the *Varroa destructor* mite.

BACKGROUND

The significant mortality of bees, who are pollinators essential to enabling plant species in the world to reproduce, is a major environmental and societal problem (see information Report No. 474 of the Senate dated Mar. 22, 2017 on "The fight against the decline of pollinators" and the Sustainable Beekeeping Development Plan). Today, 20,000 plant species are affected by the disappearance of bees and 40% of our diet directly depends on them.

Agricultural sectors and fruit, vegetable and seed producers are also directly impacted by their decline.

There are numerous causes of this decline (pesticides, Asian hornet, bacteria, fungi, mites, etc.). However, the *Varroa destructor* mite, which appeared in France in 1982, constitutes a major problem for beekeeping all over the world. These mites grow on the bees and their larvae causing malformations, and weak bees, who are more vulnerable to bacteria, fungi (such as *Nosema ceranae*) and other diseases. These multiple factors result in high mortality of bee colonies worldwide that can reach up to 90% per year in some regions of the world. It is accepted that highly affected colonies cannot survive. Treatments exist, but they are currently based on toxic and probably carcinogenic acaricides, which themselves can decimate colonies and contaminate the honey, wax and consumer at the end of the chain. These treatments are therefore exclusively used during the winter period or during periods when honey is not produced.

To date, there are two types of products on French and European markets: veterinary products for drug treatment against *Varroa destructor* and feeding products for bees comprising nutritional elements, often based on sugars, proteins, vitamins, and/or biomass extracts.

Veterinary products to fight against *Varroa destructor* often comprise toxic, carcinogenic, teratogenic molecules that can find their way into honey and wax.

Recently, Ziegelmann et al. (*Scientific Reports* 2018, 8, DOI: https://doi.org/10.1038/s41598-017-19137-5) describe that lithium chloride has an effect against *Varroa destructor* by systemic mode of action when the compound is administered at a concentration between 2 mM and 25 mM for at least 24 hours. Until now, lithium salts have been used as antidepressant substances in humans. The accumulation thereof in humans, when it exceeds a certain level, may be toxic. Various results from in vivo or in vitro studies show that the toxicity of lithium appears in serum lithium concentrations greater than 2 mmol/l. The use of lithium chloride at a high concentration could cause a health risk both for beekeepers and for consumers.

On the other hand, feeding products for bees are non-toxic to bees and humans because they essentially comprise elements of natural origin, such as sugars, proteins, vitamins, and/or biomass extracts. However, the effectiveness of these products in increasing the production of honey is not scientifically proven. These products available on the market do not show any effect in terms of protecting bees and larvae against *Varroa destructor* infestation.

Molybdenum is a trace element essential to life on Earth, both for plants and for animals or humans. It is also naturally present in bees (approximately 40 ng/bee according to our studies).

Moldovan patent MD4438 describes a feeding method for bees using the compound [tetraoxo-ethylenediaminetetraacetato-dimolybdate (V)] of bis-(tetraphenylphosphonium) di-hemihydrate (denoted $PPh_4$-$[Mo_2O_4]$-EDTA), as well as a method of producing same. This compound shows an effect of stimulating the oogenesis functions of the queens, increasing the amount of larvae, improving the quantitative development of the bee families and increasing productivity thereof.

The production of new food supplements to help bees combat these external attacks may also make it possible to reduce mortality in domestic bee colonies.

This mortality is particularly high during the winter period. This winter mortality varies depending on the region of the world. In California, this mortality may reach a record level of 80% depending on the years, which is high.

Thus, the expectations of beekeepers remain extremely high for new non-toxic products that make it possible to:
  significantly reduce the mortality of bee colonies, particularly during the winter period,
  combat the *Varroa destructor* parasite throughout the year,
  promote the development of colonies,
  increase honey production, in a context of reduced global production while there is an increase in demand.

It is therefore necessary to develop new non-toxic products making it possible both to effectively stimulate the growth of bees and increase the productivity of honey, protect bees and larvae from *Varroa destructor* and finally reduce the mortality, particularly winter mortality, of bee colonies.

SUMMARY

The inventors have developed a family of formula I molybdenum complexes:

$$A1_m\text{-}[Mo_2O_2E_2]\text{-}L_n,$$

wherein:
  A1 is a cation chosen from alkali metal cations, alkaline earth metal cations, transition metal cations, or a $PPh_4^+$ organic cation
  E is selected from O or S,
  L is a ligand selected from amino acids such as glycine (gly⁻), cysteine (L-cys²⁻) or histidine (L-his⁻) or poly-carboxylate ligands such as oxalate (Ox²⁻), citrate (Cit³⁻), ethylenediaminetetraacetate (EDTA⁴⁻), nitrilo-triacetate (HNTA²⁻), and iminodiacetate (IDA²⁻),
  m is the number of cations and is selected from 0, 1, 2, 3 and 4;
  n is the number of ligands and is selected from 1 and 2.

The formula I molybdenum complexes all comprise two molybdenum atoms in the oxidation state of +V (Mo(V)), which are connected by an Mo—Mo bond and either by sulfur atoms (bridging sulfide groups S²⁻) or with oxygen atoms (bridging Oxo groups O²⁻). The coordination spheres around the Mo(V) atoms are respectively supplemented by a terminal oxo ligand that provides the core of this family of complexes: the clusters $[Mo_2O_2S_2]^{2+}$ (dioxo-di-µ-sulfido-dimolybdenum (V)) or $[Mo_2O_4]^{2+}$ (dioxo-di-µ-oxo-dimolybdenum (V)). The cluster is then supplemented by other ligands in such a way that each Mo(V) atom is either penta-or hexa-coordinated. The complexes thus supplemented are neutral or most often negatively charged. In this latter case, they are combined with cations that may be inorganic cations or an organic $PPh_4^+$ cation (tetraphenylphosphonium) to balance the charge of the complex to a zero charge.

Contrary to expectation, it is observed that feeding bees with a food supplement comprising an annual dose of the order of a few micromoles of a formula I molybdenum complex makes it possible not only to increase the production of honey and lower the winter mortality of bees, but above all, to significantly reduce the infestation of bees and/or their larvae by *Varroa destructor.*

The formula I molybdenum complexes make it possible to reduce *Varroa* infestation of colony bees to 62% and to 82% for colony larvae.

It should be noted that, to date, there is no known treatment to protect bee larvae from *Varroa.*

Furthermore, no treatment or food supplement on the market currently makes it possible to protect bee larvae from *Varroa*, promote the development of the colonies, reduce mortality, particularly winter mortality, of bees and consequently increase honey production.

Without wishing to be bound by any theory of the invention, the products do not act directly on *Varroa* but are likely to stimulate the immune system of the bees, which helps them to fight this parasite more successfully.

It is also surprising to note that formula I molybdenum complexes, when they do not comprise an organic cation, produce even more significant beneficial effects compared to the $PPh_4$-$[Mo_2O_4]$-EDTA complex previously disclosed, on the amount of honey produced during the first harvest.

Thus, the first aspect of the present invention relates to a molybdenum complex of the following formula I:

$$A1_m\text{-}[Mo_2O_2E_2]\text{-}L_n, \qquad\qquad I$$

wherein:

A1 is a cation chosen from alkali metal cations, alkaline earth metal cations, transition metal cations, or a $PPh_4^+$ organic cation E is selected from O or S, L is a ligand selected from amino acids such as glycine $(gly^-)$, cysteine $(L\text{-}cys^{2-})$ or histidine $(L\text{-}his^-)$ or polycarboxylate ligands such as oxalate $(Ox^{2-})$, citrate $(Cit^{3-})$, ethylenediaminetetraacetate $(EDTA^{4-})$, nitrilotriacetate $(HNTA^{2-})$, and iminodiacetate $(IDA^{2-})$, m is the number of cations and is selected from 0, 1, 2, 3 and 4;

n is the number of ligands and is selected from 1 and 2, for use in preventing the infestation of bees and/or larvae by the *Varroa destructor* mite.

The cation number m and the ligand number n in a formula I molybdenum complex are determined according to the following rule: the ligand(s) L in a formula I molybdenum complex make(s) it possible to supplement the clusters $[Mo_2O_2S_2]^{2+}$ or $[MB_2O_4]^{2+}$ so that each Mo(V) atom is penta- or hexa-coordinated and the cations in the formula I molybdenum complex make it possible to balance the electrical charge of the complex to a zero charge.

Consequently, the number of ligands L in a formula I molybdenum complex depends on the denticity of the ligand chosen.

For example, when ligand L is an hexadentate ligand, such as EDTA, a formula I molybdenum complex comprises a single ligand. On the other hand, two tridentate ligands such as L-cysteine, L-histidine, citrate, nitrilotriacetate, or iminodiacetate are necessary to hexacoordinate the two atoms of Mo(V) of the clusters $[Mo_2O_2S_2]^{2+}$ or $[Mo_2O_4]^{2+}$. In the case of bidentate ligands such as glycine or oxalate ion $(Ox^{2-})$, two water molecules supplement the coordination spheres around the molybdenum atoms in addition to two ligands, each of which is found in the coordination sphere of a molybdenum atom.

In the context of the present invention, "polycarboxylate ligand" is understood to mean a ligand having several carboxylate functions. As an example of a polycarboxylate ligand, mention may be made of oxalate $(Ox^{2-})$ or citrate $(Cit^{3-})$.

The number of cations in a formula I complex of the invention depends both on the charge and the number of ligands and on the valency of the cation.

For example, the cluster $[Mo_2O_2E_2]^{2+}$ supplemented by glycine $(gly^-)$ or histidine $(L\text{-}his^-)$ as a ligand has a neutral charge. Consequently, in a formula I molybdenum complex, when L is gly or L-his, said complex does not comprise any cation.

In the context of the present invention, when the presence of a cation is necessary to balance the charge of the complex to zero charge, said cation can be chosen from the cations of alkali metals, cations of alkaline-earth metals, cations of transition metals.

By way of examples of alkali metal cations that can be used in the context of the present invention, mention may be made of $Li^+$, $Na^+$, $K^+$, $Rb^+$, and $Cs^+$ By way of examples of cations of alkaline earth metals, mention may be made of $Be^{2+}$, $Mg^{2+}$, $Ca^{2+}$, $Sr^{2+}$, and $Ba^{2+}$.

By way of examples of transition metal cations, mention may be made of a cation of scandium, titanium, vanadium, chromium, manganese, iron, cobalt, nickel, copper, zinc, yttrium, palladium, silver, platinum and gold.

Each molecule of said formula I molybdenum complex can further comprise several solid-state solvation water molecules.

One embodiment of the present invention relates to a molybdenum complex of the following formula I(i):

$$A1_m\text{-}[Mo_2O_4]\text{-}L_n \qquad\qquad I(i)$$

wherein:

A1 is a cation chosen from alkali metal cations, alkaline earth metal cations, transition metal cations, or a $PPh_4^+$ organic cation, L is a ligand selected from amino acids such as glycine $(gly^-)$, cysteine $(L\text{-}cys^{2-})$ or histidine $(L\text{-}his^-)$ or polycarboxylate ligands such as oxalate $(Ox^{2-})$, citrate $(Cit^{3-})$, ethylenediaminetetraacetate $(EDTA^{4-})$, nitrilotriacetate $(HNTA^{2-})$, and iminodiacetate $(IDA^{2-})$, m is the number of cations and is selected from 0, 1, 2, 3 and 4;

n is the number of ligands and is selected from 1 and 2, for use in preventing the infestation of bees and/or larvae by the *Varroa destructor* mite.

Another embodiment of the invention relates to a molybdenum complex of the following formula I(ii):

$$A1_m\text{-}[Mo_2O_2S_2]\text{-}L_n \qquad\qquad I(ii)$$

wherein:

A1 is a cation chosen from alkali metal cations, alkaline earth metal cations, transition metal cations, or a $PPh_4^+$ organic cation, L is a ligand selected from amino acids such as glycine $(gly^-)$, cysteine $(L\text{-}cys^{2-})$ or histidine $(L\text{-}his^-)$ or polycarboxylate ligands such as oxalate $(Ox^{2-})$, citrate $(Cit^{3-})$, ethylenediaminetetraacetate $(EDTA^{4-})$, nitrilotriacetate $(HNTA^{2-})$, and iminodiacetate $(IDA^{2-})$, m is the number of cations and is selected from 0, 1, 2, 3 and 4;

n is the number of ligands and is selected from 1 and 2, for use in preventing the infestation of bees and/or larvae by the *Varroa destructor* mite.

An advantageous embodiment of the invention relates to a molybdenum complex of the following formula II:

$$A2_m\text{-}[Mo_2O_2E_2]\text{-}L_n \qquad\qquad II$$

wherein:

A2 is a cation chosen from alkali metal cations, alkaline earth metal cations, or transition metal cations, E is selected from O or S, L is a ligand selected from amino acids such as glycine (gly$^-$), cysteine (L-cys$^{2-}$) or histidine (L-his$^-$) or poly-carboxylate ligands such as oxalate (Ox$^{2-}$), citrate (Cit$^{3-}$), ethylenediaminetetraacetate (EDTA$^{4-}$), nitrilo-triacetate (HNTA$^{2-}$), iminodiacetate? (IDA$^{2-}$), m is the number of cations and is selected from 0, 1, 2, 3 and 4; n is the number of ligands and is selected from 1 and 2, for use in preventing the infestation of bees and/or their larvae by the *Varroa destructor* mite.

The formula II molybdenum complexes, which do not comprise an organic cation (PPh$_4$+), but only inorganic cations selected from alkali metal cations, alkaline earth metal cations, or transition metal cations, when the presence of cations is necessary, have more significant beneficial effects for bees and/or their larvae, whether for honey production, the prolificity of the queen, or protecting their bees and/or larvae from being attacked by the *Varroa destructor* mite.

As examples of advantageous inorganic cations for the formula II molybdenum complex, mention may be made of Na$^+$, K$^+$, Li$^+$, Ca$^{2+}$, Mg$^{2+}$, and Zn$^{2+}$.

In one particular embodiment, the invention is implemented by the molybdenum complexes of formula I, I(i), I(ii), or II in which the ligand is selected from cysteine (L-cys$^{2-}$), polycarboxylate ligands such as oxalate (Ox$^{2-}$), citrate (Cit$^{3-}$), ethylenediaminetetraacetate (EDTA$^{4-}$), nitrilotriacetate? (HNTA$^{2-}$), and iminodiacetate? (IDA$^{2-}$), the number of ligands n being selected from 1 and 2, the number of cations m being selected from 1, 2, 3 and 4.

In a more particular embodiment, the invention is implemented by the molybdenum complexes of formula II, wherein:

A2 is a cation selected from Na$^+$, K$^+$, Li$^+$, Ca$^{2+}$, Mg$^{2+}$, and Zn$^{2+}$, E is selected from O or S, L is a ligand selected from cysteine (L-cys$^{2-}$), polycarboxylate ligands such as oxalate (Ox$^{2-}$), citrate (Cit$^{3-}$), ethylenediaminetetraacetate (EDTA$^{4-}$), nitrilotriacetate (HNTA$^{2-}$), and iminodiacetate (IDA$^{2-}$), m is the number of cations and is selected from 1, 2, 3 and 4;

n is the number of ligands and is selected from 1 and 2.

In a particular embodiment of the invention, the molybdenum complexes of formula I for use in preventing the *Varroa destructor* mite are selected from Na$_2$[Mo$_2$O$_4$(EDTA)]·xH$_2$O (x=5-6), Li$_2$[Mo$_2$O$_4$(EDTA)]·xH$_2$O (x=3-6), and (PPh$_4$)$_2$[Mo$_2$O$_4$(EDTA)]·xH$_2$O (x=2-5).

In order to efficiently protect bees and/or larvae from the *Varroa destructor* mite, it is advisable to use at least one molybdenum complex of formula I, I(i), II(ii) or II in an annual quantity of 1 to 60 mg/bee colony, especially from 1 to 40 mg/bee colony, even especially from 1 to 20 mg/bee colony, even more especially from 1 to 15 mg/bee colony, even especially from 1 to 10 mg/bee colony, even especially from 1 to 8 mg/bee colony, even especially from 1.5 to 8 mg/bee colony, and more particularly from 2 to 6 mg/bee colony.

These annual amounts correspond to an order of a few micromoles of the complex of formula I, I(i), I(ii) or II.

"An annual amount" is understood to mean an overall amount administered to a bee colony within a period of 12 successive months.

The administration can be carried out by a single dose or by several doses according to a feeding protocol.

The term "bee colony" is understood to mean a group of bees that population the hive and formed by 3 types of bees, namely a single queen, who is a sexual female, several thousand workers who are asexual females and a few dozen false drones who are male.

The terms "bee colony" and "a swarm of bees" are interchangeable.

The molybdenum complexes of formula I, I(i), I(ii), or II as described above may be used to prevent *Varroa destructor* infestations for all breeds of domestic bees intended for beekeeping, especially for breeds of European domestic bees.

In order to be administered to bees, said molybdenum complex of formula I, I(i), I(ii) or II can be incorporated into a food supplement for bees in the form of a powder, a syrup, a paste or an aqueous solution.

One or several molybdenum complexes of formula I, I(i), I(ii) or II can be mixed with one or more foods for bees, such as water, pollen, nectar, honey, sugars, vitamins, minerals, lipids, and proteins.

In one particular embodiment of the invention, several different molybdenum complexes of formula I, I(i), I(ii) or II can be used at the same time.

Another aspect of the present invention relates to a composition comprising at least one molybdenum complex of the following formula I:

$$A1_m\text{-}[Mo_2O_2E_2]\text{-}L_n \qquad\qquad I$$

wherein:

A1 is a cation chosen from alkali metal cations, alkaline earth metal cations, transition metal cations, or a PPh$_4^+$ organic cation E is selected from O or S, L is a ligand selected from amino acids such as glycine (gly$^-$), cysteine (L-cys$^{2-}$) or histidine (L-his$^-$) or poly-carboxylate ligands such as oxalate (Ox$^{2-}$), citrate (Cit$^{3-}$), ethylenediaminetetraacetic acid (EDTA$^{4-}$), nitrilotriacetate (HNTA$^{2-}$), and iminodiacetate (IDA$^{2-}$), m is the number of cations and is selected from 0, 1, 2, 3 and 4;

n is the number of ligands and is selected from 1 and 2, for use in preventing the infestation of bees and/or their larvae by the *Varroa destructor* mite.

The aforesaid composition can further comprise one or more foods for bees selected from water, pollen, nectar, honey, sugars, vitamins, minerals, lipids, and proteins.

Said composition may be in the form of an aqueous solution, a concentrate, a paste, a syrup, or in the form of a water-soluble powder.

The person skilled in the art can adapt the form of the composition depending on the feeding period, frequency and/or objective.

In a more particular embodiment of the aforesaid composition for preventing the infestation of bees and/or their larvae by the *Varroa destructor* mite, said molybdenum complex corresponds to the following formula I(i):

$$A1_m\text{-}[Mo_2O_4]\text{-}L_n \qquad\qquad I(i)$$

wherein:

A1 is a cation chosen from alkali metal cations, alkaline earth metal cations, transition metal cations, or a $PPh_4^+$ organic cation, L is a ligand selected from amino acids such as glycine $(gly^-)$, cysteine $(L\text{-}cys^{2-})$ or histidine $(L\text{-}his^-)$ or polycarboxylate ligands such as oxalate $(Ox^{2-})$, citrate $(Cit^{3-})$, ethylenediaminetetraacetate $(EDTA^{4-})$, nitrilotriacetate $(HNTA^{2-})$, and iminodiacetate $(IDA^{2-})$, m is the number of cations and is selected from 0, 1, 2, 3 and 4;

n is the number of ligands and is selected from 1 and 2.

In another more particular embodiment of the aforesaid composition for preventing the infestation of bees and/or their larvae by the *Varroa destructor* mite, said molybdenum complex corresponds to the following formula I(i):

$$A1_m\text{-}[Mo_2O_2S_2]\text{-}L_n \qquad\qquad I(ii)$$

wherein:

A1 is a cation chosen from alkali metal cations, alkaline earth metal cations, transition metal cations, or a $PPh_4^+$ organic cation, L is a ligand selected from amino acids such as glycine $(gly^-)$, cysteine $(L\text{-}cys^{2-})$ or histidine $(L\text{-}his)$ or polycarboxylate ligands such as oxalate $(Ox^{2-})$, citrate $(Cit^{3-})$, ethylenediaminetetraacetic acid $(EDTA^{4-})$, nitrilotriacetate $(HNTA^{2-})$, iminodiacetate $(IDA^{2-})$, m is the number of cations and is selected from 0, 1, 2, 3 and 4;

n is the number of ligands and is selected from 1 and 2.

for use in preventing the infestation of bees and/or their larvae by the *Varroa destructor* mite.

In a more particular embodiment of the invention, said composition comprises a formula I(i) molybdenum complex selected from $Na_2[Mo_2O_4 \ (EDTA)]\cdot xH_2O$ (x=5-6), $Li_2[Mo_2O_4 \ (EDTA)]\cdot xH_2O$ (x=3-6), and $(PPh_4)_2[Mo_2O_4 (EDTA)]\cdot xH_2O$ (x=2-5).

In another particular embodiment of the aforesaid composition for preventing the infestation of bees and/or their larvae by the *Varroa destructor* mite, said molybdenum complex corresponds to the following formula II:

$$A2_m\text{-}[Mo_2O_2E_2]\text{-}L_n, \qquad\qquad II$$

wherein:

A2 is a cation chosen from alkali metal cations, alkaline earth metal cations, or transition metal cations, E is selected from O or S, L is a ligand selected from amino acids such as glycine $(gly^-)$, cysteine $(L\text{-}cys^{2-})$ or histidine $(L\text{-}his^-)$ or polycarboxylate ligands such as oxalate $(Ox^{2-})$, citrate $(Cit^{3-})$, ethylenediaminetetraacetic acid $(EDTA^{4-})$, nitrilotriacetate $(HNTA^{2-})$, and iminodiacetate $(IDA^{2-})$ m is the number of cations and is selected from 0, 1, 2, 3 and 4;

n is the number of ligands and is selected from 1 and 2.

In a more particular embodiment of the invention, said composition comprises a formula II molybdenum complex having a cation selected from $Na^+$, $K^+$, $Li^+$, $Ca^{2+}$, $Mg^{2+}$, and $Zn^{2+}$.

In an even more particular embodiment of the invention, said composition comprises a formula II molybdenum complex, having a cation selected from $Na^+$, $K^+$, $Li^+$, $Ca^{2+}$, $Mg^{2+}$, and $Zn^{2+}$, and a ligand L selected from cysteine $L\text{-}cys^{2-}$), polycarboxylate ligands such as oxalate $(Ox^{2-})$, citrate $(Cit^{3-})$, ethylenediaminetetraacetic acid $(EDTA^{4-})$, nitrilotriacetate $(HNTA^{2-})$, and iminodiacetate $(IDA^{2-})$, the number of cations m being selected from 1, 2, 3, and 4; and the number of ligands n being selected from 1 and 2.

The subject matter of the present invention is also a method for preventing the infestation of bees and their larvae by the *Varroa destructor* mite.

Said method comprises or consists of feeding the colony with a molybdenum complex of formula I, I(i), I(ii), or II, as defined previously or a composition comprising a molybdenum complex of formula I, I(i), I(ii), or II, as defined previously, the overall annual amount of said complex used per colony being from 1 to 60 mg/bee colony, especially from 1 to 40 mg/bee colony, even especially from 1 to 20 mg/colony, even especially from 1 to 10 mg/bee colony, even especially from 1 to 8 mg/bee colony, even especially from 1.5 to 8 mg/bee colony, and more particularly from 2 to 6 mg/bee colony.

Said prevention method can be implemented by a single dose.

In a particular embodiment of said method, each colony is fed with a molybdenum complex of formula I, I(i), I(ii) or II, as defined previously or with a composition comprising a molybdenum complex of formula I, I(i), I(ii), or II, as defined previously, at a single dose of 1 to 60 mg/bee colony, especially from 1 to 40 mg/bee colony, even especially from 1 to 20 mg, even especially from 1 to 10 mg/bee colony, even especially from 1 to 8 mg/bee colony, even especially from 1.5 to 8 mg/bee colony, and more particularly from 2 to 6 mg/bee colony.

Said prevention method can also be carried out by several doses according to a protocol in order to reach the overall annual quantity of a complex of formula I, I(i), I(ii) or II, from 1 to 60 mg/bee colony, especially from 1 to 40 mg/bee colony, even especially 1 to 20 mg/bee colony, even especially from 1 to 10 mg/bee colony, even especially from 1 to 8 mg/bee colony, even especially from 1.5 to 8 mg/bee colony, and more particularly from 2 to 6 mg/bee colony.

The feeding frequency and the amount of the complex for each feed can be adapted according to the overall annual amount to be administered.

For example, each colony may be fed with a molybdenum complex of formula I, I(i), I(ii), or II as defined previously or with a composition comprising a molybdenum complex of formula I, I(i), I(ii), or II, as defined previously, at an amount of a molybdenum complex of 0.1 to 1 mg/colony every other day for 20 days, to achieve an overall amount of 1 to 10 mg/colony.

The period of implementation of said prevention method can be any period of the year, but preferably the period between autumn and spring.

For example, to prepare the colony for the winter period, the colony should be fed in autumn with a syrup comprising a molybdenum complex of formula I, I(i), I(ii) or II or a composition as defined previously in syrup form. This feeding can be carried out as soon as the temperatures drop below approximately 10° C.

Furthermore, in order to stimulate the bees for the new beekeeping season, it is possible to feed the bees either in January with a candy loaf comprising a molybdenum complex of formula I, I(i), I(ii) or II or a composition as defined previously in the form of a candy loaf, that is at the start of spring with a syrup comprising a molybdenum complex of formula I, I(i), I(ii) or II or a composition as defined previously in syrup form.

The candy loaf for winter feeding can be quantified in order to be consumed for several months over the winter period Speculative feeding that is done at the start of spring makes it possible to simulate honeyflow and bring forward the arrival of the first generation of bees of the season. In general, speculative nourishment is carried out approximately 30-40 days before the expected arrival of the first flowers in nature.

The present invention also relates to a food supplement for bees.

Said food supplement comprises a molybdenum complex of the following formula II:

$$A2_m\text{-}[Mo_2O_2E_2]\text{-}L_n, \qquad II$$

wherein:

A2 is a cation chosen from alkali metal cations, alkaline earth metal cations, or transition metal cations, E is selected from O or S, L is a ligand selected from amino acids such as glycine (gly$^-$), cysteine (L-cys$^{2-}$) or histidine (L-his$^-$) or polycarboxylate ligands such as oxalate (Ox$^{2-}$), citrate (Cit$^{3-}$), ethylenediaminetetraacetic acid (EDTA$^{4-}$), nitrilotriacetate (HNTA$^{2-}$), and iminodiacetate (IDA$^{2-}$)

m is the number of cations and is selected from 0, 1, 2, 3 and 4;

n is the number of ligands and is selected from 1 and 2.

"Food supplement for bees" is understood to mean additional food to the natural food collected by bees, said food supplement being supplied to the bees by means of suitable feeding methods. The food supplements for bees comprise the essential nutrients for bees to overcome the nutritional deficiencies of bees and/or to strengthen the immune defenses of bees.

In one particular embodiment, said food supplement for bees of the invention comprises a molybdenum complex represented by formula II(i) $A2_m\text{-}[Mo_2O_4]\text{-}L_n$ or by formula II(ii) $A2_m\text{-}[Mo_2O_2S_2]\text{-}L_n$, A2, L, m and n being as defined for formula II.

In another particular embodiment, said food supplement for the bees of the invention comprises a molybdenum complex of formula II, II(i) or II(ii), wherein A2 is a cation selected from Li$^+$, Na$^+$, K$^+$, Ca$^{2+}$, Mg$^{2+}$ and Zn$^{2+}$.

In another particular embodiment, said food supplement for the bees of the invention comprises a molybdenum complex of formula II, II(i) or II(ii) selected from Na$_2$[Mo$_2$O$_4$ (EDTA)]·xH$_2$O, Li$_2$[Mo$_2$O$_4$ (EDTA)]·xH$_2$O, K$_2$[Mo$_2$O$_2$S$_2$ (LCys)$_2$]·xH$_2$O, Na$_2$[Mo$_2$O$_4$ (LCys)$_2$]·xH$_2$O, K$_2$[Mo$_2$O$_2$S$_2$](HNTA)$_2$]·xH$_2$O, K$_2$[Mo$_2$O$_2$S$_2$ (EDTA)]·xH$_2$O, K$_2$[Mo$_2$O$_4$ (HNTA)$_2$]·xH$_2$O, Mg [Mo$_2$O$_4$ (EDTA)]·xH$_2$O, Ca [Mo$_2$O$_4$ (EDTA)]·xH$_2$O, and Zn [Mo$_2$O$_4$ (EDTA)]·xH$_2$O with x generally between 2 and 6.

Said food supplement further comprises one or more foods for bees selected from water, pollen, nectar, honey, sugars, vitamins, minerals, lipids, and proteins, in order to provide the amino acids, vitamins, fatty acids and trace elements essential to the health of the bee.

Depending on the way in which the feed is carried out, said food supplement of the invention can be in the form of a powder, a syrup, a paste or an aqueous solution.

For example, for speculative feeding that is performed in the spring and that serves to stimulate egg laying by the queen, the food supplement of the invention can be in the form of a sugar syrup. For scheduled feeding of the supplement at the beginning of autumn or carried out during the winter, said food supplement of the invention may be in the form of a sugar paste product.

Said nutritional supplement of the invention can be in the form of a concentrate to be diluted in a syrup.

The amount of a molybdenum complex of formula II, II(i) or II(ii) in a food supplement of the invention can be adapted according to the type of product, the feeding means, and the feeding frequency such that the overall annual amount of said complex used per colony is 1 to 60 mg/colony, especially 1 to 40 mg/colony, even especially 1 to 20 mg/colony, even especially 1 to 10 mg/bee colony, even especially 1 to 8 mg/bee colony, even more particularly 1.5 to 8 mg/bee colony, and more particularly from 2 to 6 mg/bee colony.

The present invention also relates to a method for feeding bees, said method comprising or consisting of feeding the bee colony with a food supplement comprising a molybdenum complex of formula II, II(i) or II(ii) as described previously, such that the overall annual amount of said complex used per colony is from 1 to 60 mg/colony, especially from 1 to 40 mg/colony, even especially from 1 to 20 mg/colony, even especially from 1 to 10 mg/bee colony, even especially from 1 to 8 mg/bee colony, even especially from 1.5 to 8 mg/bee colony, and more particularly from 2 to 6 mg/bee colony.

Said method can be implemented during any period of the year, but preferably in autumn, in order to prepare the colony for winter, or in the spring to stimulate the bees.

For example, to prepare the colony for the winter period, the colony should be fed in autumn with a syrup comprising a molybdenum complex of formula I, I(i), I(ii) or II or a composition as defined previously in syrup form. This feeding can be carried out as soon as the temperatures drop below approximately 10° C.

Furthermore, in order to stimulate the bees for the new beekeeping season, it is possible to feed the bees either in January with a candy loaf comprising a molybdenum complex of formula I, I(i), I(ii) or II or a composition as defined previously in the form of candy loaf, that is at the start of spring with a syrup comprising a molybdenum complex of formula I, I(i), I(ii) or II or a composition as defined previously in syrup form.

The candy loaf for winter feeding can be quantified in order to be consumed for several months over the winter period.

Speculative feeding that is done at the start of spring makes it possible to simulate honeyflow and bring forward the arrival of the first generation of bees of the season. In general, speculative nourishment is carried out approximately 30-40 days before the expected arrival of the first flowers in nature.

Without wishing to be bound by any theory of the invention, said method could strengthen the immune system of the bees and larvae, which makes it possible to increase honey production, and in particular lower winter mortality when it is applied in the autumn.

Thus, the subject matter of the present invention is also a food supplement for bees comprising a molybdenum complex of formula II as defined above, for use in reducing the mortality of bee colonies, in particular winter mortality.

Finally, the subject matter of the present invention is the use of a food supplement for bees comprising a molybdenum complex of formula II as defined above, in order to increase the production of honey by bees, especially the production of honey during the first harvest.

BRIEF DESCRIPTION OF THE FIGURES

The present invention is illustrated in more detail in the figures and examples below.

FIG. 1: Chemical structures of the cluster $[Mo_2O_2S_2]^{2+}$ or $[Mo_2O_4]^{2+}$ supplemented by $EDTA^{4-}$, $HNTA^{2-}$, $NTA^{3-}$, or L-$Cys^{2-}$. In FIG. 1: Mo (gray, cross-hatching), O (gray, vertical hatching), S (gray, horizontal hatching), N (gray, oblique hatching), C (black), H (white).

FIG. 2A: Survival curves for bees of a known age, in cages, fed with 20 mg/L of Na—$Mo_2O_4$-EDTA in a sugary food solution.

The line with the symbol ■ corresponds to the group fed with a solution containing Na—$Mo_2O_4$-EDTA.

The line with the symbol □ corresponds to the control group fed with a sucrose solution.

The dotted line indicates the start of feeding with the solution containing Na—$Mo_2O_4$-EDTA for the treated group. (20 mg/L: n=50+/−3 for each group).

FIG. 2B: Survival curves for bees of a known age, in cages, fed with 2 mg/L of Na—$Mo_2O_4$-EDTA in a sugary food solution.

The line with the symbol ■ corresponds to the group fed with a solution containing Na—$Mo_2O_4$-EDTA.

The line with the symbol □ corresponds to the control group fed with a sucrose solution.

The dotted line indicates the start of feeding with the solution containing Na—$Mo_2O_4$-EDTA for the treated group.

The experiment was repeated on 3 groups of bees. Each group had 50 bees.

DETAILED DESCRIPTION

EXAMPLES

1. Synthesis of the Formula I Molybdenum Complexes

The methods for synthesizing two complexes of formula I, $Na_2[Mo_2O_4$ (EDTA)]·$5H_2O$ and $Li_2[MB_2O_4EDTA]$·$6H_2O$, are described below. The synthesis of the compound $(PPh_4)_2[Mo_2O_4$ (EDTA)]·$2.5H_2O$, denoted $PPh_4$-$Mo_2O_4$-EDTA, has been disclosed in patent MD4438.

Synthesis of $Na_2[Mo_2O_4$ (EDTA)]·$5H_2O$, denoted Na—$Mo_2O_4$-EDTA; Mm=680.15 g/mol Sodium molybdate dihydrate $Na_2MoO_4$*$2H_2O$ (2.92 g, 12.07 mmol) and $Na_2H_2EDTA$*$2H_2O$ (2.25 g, 6.04 mmol) is dissolved in 30 mL of distilled water. An aqueous hydrazinium sulfate solution $N_2H_4$*$H_2SO_4$ (785.96 mg, 6.04 mmol/10 ml of water) is added and a 1M HCl solution is used to adjust the pH to 3 in order to allow the reduction of $[Mo^{(VI)}O_4]^{2-}$ into $[Mo^{(V)}_2O_4]^{2+}$. The dark red solution obtained is heated to 80° C. for one and a half hours with continuous stirring. After cooling to ambient temperature, the solution is transferred to a crystallizer and left to evaporate. After a few days, red crystals of the pure product $Na_2[Mo_2O_4$ (EDTA)]·$5H_2O$ are collected by filtration, washed quickly in cold water and left to air dry. The yield is thus 65%. The product is characterized by FT-IR, elemental analysis, TGA, ESI-MS, EDX and RMN. FT-IR (v, $cm^{-1}$): 3518 (m), 3300 (m), 1645 (s), 1445 (w), 1384 (m), 1350 (s, sh.), 1243 (w), 972 (w), 944 (m), 911 (w), 863 (w), 761 (w); Elemental analysis for $Na_2[MO_2O_4$ $(C_{10}H_{12}N_2O_8)]$· $5H_2O$ Calculated (found): C, 17.66 (17.42) H, 3.26 (2.92) N, 4.12 (4.18); EDX: expected atomic ratio (found) Mo/Na 1.00 (1.05); ESI-MS m/z 272.05 (m/z calculated for $[Mo_2O_4$ (EDTA)$_2]^{2-}$ 271.93); TGA analysis shows 13.3% weight loss in the temperature range of 25-200° C. corresponding to the hydration water (calculated 13.2%); $^1$H-NMR (δ ppm, 400 MHz, $D_2O$) 2.61 (m, wide, 4H), 3.40 (m, wide, 8H).

Synthesis of $Li_2[Mo_2O_4$ (EDTA)]·$6H_2O$, denoted Li—$Mo_2O_4$-EDTA; Mm=666.07 g/mol The compound $Li_2[Mo_2O_4$ (EDTA)]·$6H_2O$ is obtained by exchanging $Na^+$ cations of the compound $Na_2[Mo_2O_4$ (EDTA)]·$5H_2O$ with Lit on a DOWEX cation exchange resin loaded with Lit cations. To do this, 1 g of $Na_2[Mo_2O_4$ (EDTA)]·$5H_2O$ is dissolved in a minimum volume of water (10 mL) and this concentrated solution is passed over a resin-loaded column. An aqueous solution of the lithium salt $Li_2[Mo_2O_4$ (EDTA)] is obtained. This latter is spray dried under reduced pressure in a rotary evaporator to obtain the desired solid product. 90% yield. The product is characterized by FT-IR, elemental analysis, TGA, ESI-MS, EDX and RMN. (n=90%). FT-IR (v, $cm^{-1}$): 3412 (s, br.), 2983 (w), 1651 (s), 1625 (s), 1446 (w), 1392 (m), 1357 (m), 1244 (w), 964 (m), 948 (w), 933 (w), 909 (w), 861 (w), 759 (w), 475 (w); Elemental analysis for $Li_2[Mo_2O_4$ $(C_{10}H_{12}N_2O_8)]$·$6H_2O$ Calculated (found): C, 18.03 (17.79) H, 3.63 (3.38) N, 4.21 (4.10); EDX: expected atomic ratio (found) Mo 100% (100%). No trace of Na proving that the cation exchange definitely occurred; ESI-MS m/z 272.05 $[Mo_2O_4$ (EDTA)$_2]^{2-}$ (271.92); The TGA shows 14.83% weight loss in the temperature range of 25-200° C. corresponding to the hydration water (calculated 13.9%); $^1$H-NMR (δ ppm, 300 MHz, $D_2O$) 2.54 (m, wide, 4H), 3.33 (m, wide, 8H).

2. Toxicity of Formula I Complexes

The toxicity of formula I complexes was assessed using 3 different methods: in vitro tests on cells, on protozoa and directly on bees.

2.1 In Vitro Cytotoxicity Study

For cell culture, human cervical epithelial cells of the HeLa line, human epithelial pancreatic adenocarcinoma cells of the BxPC-3 line and healthy Madin-Darby canine kidney epithelial cells of the MDCK line were used in this study. The Resazurin cell proliferation test was applied according to the literature (S. Anoopkumar-Dukie, J. B. Carey, T. Conere, E. O'Sullivan, F. N. van Pelt, A. Allshire, Br J Radiol 2005, 78, 945, DOI: 10.1259/bjr/54004230). As an indicator of the effectiveness of the experimental compounds on cell proliferation, the median inhibitory concentration ($IC_{50}$) was used. The lower the $IC_{50}$ value, the higher the activity (in this case, the cytotoxicity). For $IC_{50}$ values equal to and greater than 100 μM, it is considered that there is no activity.

Five formula I complexes were tested in this study in comparison to two reference anti-cancer compounds ("Cisplatin" and Doxorubicin complex).

The results of the tests are given in Table 1 below.

TABLE 1

| Compound | $IC_{50}$, μM | | |
| --- | --- | --- | --- |
| | MDCK | BxPc-3 | HeLa |
| $PPh_4$—$Mo_2O_4$-EDTA | 60.72 ± 12.1 | 25.09 ± 7.02 | ≥100 |
| Na—$Mo_2O_4$-EDTA | Inactive | Inactive | Inactive |
| Li—$Mo_2O_4$-EDTA | Inactive | Inactive | Inactive |
| $PPh_4$—$Mo_2O_2S_2$-EDTA | ≥100 | 59.81 ± 26.45 | ≥100 |
| K—$Mo_2O_2S_2$-Cys | Inactive | Inactive | Inactive |
| Cisplatin (ref. 1) | 30.9 ± 1.1 | 11.2 ± 1.2 | 3.99 ± 0.33 |
| Doxorubicin (ref. 2) | 1.48 ± 3.1 | 3.99 ± 7.9 | 1.31 ± 4.9 |

Cytotoxicity of compounds on healthy cells (MDCK), pancreatic cancer (BxPc-3) and cervical cancer cells (HeLa).

Table 1 shows that the compounds studied are mostly non-cytotoxic. Compounds with the counter cations, $PPh_4^+$, show a low activity related to the organic cation itself. Nevertheless, the $IC_{50}$ gives concentrations at least 100 times greater than those used in hives (of the order of 0.2-0.6 UM). Na—$Mo_2O_4$-EDTA and Li—$Mo_2O_4$-EDTA salts have no cytotoxicity.

2.2 Toxicity Study on Protozoa.

This study was also conducted by researchers of the Department of Chemistry from Moldova State University. Compounds which showed no in vitro toxicity on cells were used in other tests on simple single-cell microorganisms, namely protozoa. The spectrophotometric method was used to evaluate the toxicity of biologically active substances relative to a paramecium culture using the NR dye, according to the protocol described in the literature (1. Zhang, S. Z., Lipsky, M. M., Trump, B. F., Hsu, I. C. Neutral red (NR) assay for cell viability and xenobiotic-induced cytotoxicity in primary cultures of human and rat hepatocytes. Cell Biol Toxicol. 1990; 6 (2): 219-34; 2. Repetto, G., del Peso, A., Zurita, J. L. Neutral red uptake assay for the estimation of cell viability/cytotoxicity. Nat Protoc 3:1125-1131.). At the end, the $LC_{50}$ value (median lethal concentration) is determined. The results of the tests are given in Table 2.

TABLE 2

| Compound | $LC_{50}$, µM | |
| --- | --- | --- |
| | 24 hours | 48 hours |
| $PPh_4$—$Mo_2O_4$-EDTA | ≥100 | ≥100 |
| Na—$Mo_2O_4$-EDTA | ≥100 | ≥100 |
| Li—$Mo_2O_4$-EDTA | ≥100 | ≥100 |
| $PPh_4$—$Mo_2O_2S_2$-EDTA | 40.25 ± 5.5 | ≥100 |
| K—$Mo_2O_2S_2$-Cys | ≥100 | ≥100 |

Toxicity of compounds on Paramecium protozoa microorganisms

An $LC_{50}$ less than 100 µM reflects high toxicity. On the other hand, a value≥100 indicates that there is no toxic effect on the development of Paramecium microorganisms. Of the 5 compounds tested, only one has slight activity that quickly disappears. The 5 compounds tested are deemed to be non-toxic.

2.3 Toxicity Study on Bees.

Additional tests on the impact on the lifespan of bees were carried out.

Fifty newly hatched bees (age=1 day) were placed in a special cage with a wax strip, water and food, and were kept in the laboratory oven at a constant temperature of 33° C. and 50% humidity. A control group of bees was fed with a solution containing only sucrose; one group of bees was fed with a solution containing sucrose and 2 mg/L of Na—$Mo_2O_4$-EDTA; another group of bees was fed with a solution containing sucrose and 20 mg/L of Na—$Mo_2O_4$-EDTA. The consumption of water and food was checked every day. Dead bees were counted and removed. For statistical reasons, the experiments were repeated up to 3 times if necessary.

There is no significant difference between the control group and the treated group fed respectively with a solution containing 2 mg/L of Na—$Mo_2O_4$-EDTA (p>0.05, $\chi^2$=3.36, ddl=1) (FIG. 2B) or a solution containing 20 mg/L of Na—$Mo_2O_4$-EDTA (p>0.05, $\chi^2$=0.04, ddl=1) (FIG. 2A).

This study confirms that Na—$Mo_2O_4$-EDTA does not induce bee mortality at 2 mg/L nor at 20 mg/L.

This test clearly shows the non-toxicity of the complex $[Mo_2O_4 (EDTA)]^{2-}$ on bees.

3. Chemical Stability of Formula I Complexes

In solid form, the compounds obtained are perfectly stable in air and can be kept without any special conditions for years without any alteration.

The stabilities of the complexes in solution are studied by different techniques ($^1$H-NMR or UV-vis spectroscopy), the objective being to study their behavior in different media in terms of stability.

The stability experiments in water in the $5 \times 10^{-3}$-$2 \times 10^{-7}$ M concentration range reveal the fact that EDTA complexes ($[Mo_2O_2S_2$-EDTA$]^{2-}$ and $[Mo_2O_4$-EDTA$]^{2-}$) show no sign of decomposition in water, which suggests very high chemical stability. In the case of K—$Mo_2O_2S_2$-LCys, it is also possible to reduce down to micromolar concentrations without any breakdown, which also suggests good chemical stability. This means that these compounds do not undergo structural modifications under high dilution conditions. The aqueous solutions of these complexes prove to be particularly stable over time.

In a physiological medium or in a sugar syrup with 50% by weight, the complexes $[Mo_2O_2S_2$-EDTA$]^{2-}$ and $[Mo_2O_4$-EDTA$]^{2-}$ (Na and Li salts) and K—$Mo_2O_2S_2$-L-Cys also show good stability at very low concentrations.

In conclusion, the formula I complexes prove to be particularly stable in different media and at high dilution.

4. Tests on Formula I Complexes in Hives

4.1. $1^{st}$ Test in Hives

Protocols Used, Parameters Monitored, and Methods Used

Biological field tests were performed on families of European domestic bees of the species *Apis mellifera carpatica* in an experimental apiary located in the Ghidighici forestry district (Republic of Moldova). Feeding with the complex of the invention took place in spring. The biological tests were monitored up to the month of September.

To administer the compounds to the bees, a very small amount of bioactive substance was added to two types of sugary feeding products for bees: candy in the form of a paste (70% sucrose, 30% honey) or syrup (50% sucrose, 50% water). The bees were fed by adding the candy/syrup to the feeder located in the inner upper part of the hive. The volume of syrup was adjusted based on the number of bee frames at the initial time, more precisely 200 g of candy per frame and 100 mL of syrup per frame, that is 2 kg of candy and 1 L of syrup per hive of 10 frames.

For the first feeding step, candy in the form of a paste was only given once. Next, for the main feed, determined volumes of syrup were used several times to feed the bees every two days for a period of two weeks, which corresponds to an annual feed quantity of approximately 2 mg to 6 mg of each compound for each hive. From the start of the test to the end (after the second harvest), all the bees were monitored for several key morpho-producing parameters that reflect the development level of the colony and the vital aspects of the bees. The parameters studied are: the prolificity of the queen (fertility), the power of the colonies, the production of honey and the production of wax. These parameters were monitored in line with the zootechnical standards concerning the assessment of bee families, breeding and certification of beekeeping parental material approved by government decision No. 306 dated Apr. 28, 2011 of the Republic of Moldova.

Assessment of Honey Production:

The production of honey (in kg) was determined for each family of bees by adding the amount of honey produced (honey from supers), extracted during the harvest season, to the amount of honey built up in the honeycomb (brood chamber) and left as food for the bees for the winter period (brood honey). The amount of honey produced will be determined for each family, for each extraction, by weighing the frames/honeycomb before and after extraction (with an accuracy of 0.1 kg), the weight difference being the quantity of honey produced that was extracted. The amount of honey left in the honeycomb to feed the bees was determined at the autumn visit (September), by weighing the honey frames and deducting (from their total weight) the total weight of the standard honeycomb frames; for Dadant type frames (435×300 mm)—0.6 kg, for Langstroth frames (435×230 mm)—0.5 kg.

Assessment of the Power of the Colony:

The power of the bee colony represents the number of bees present in the honeycomb at the time of the assessment. The assessment is performed three times per year: at the spring visit (March-April), at the end of spring (20-31 May) and at the visit in autumn (September). After these three assessments, the average power of the bee family is determined. The amount of bees (kg) is determined by multiplying the number of intervals between the frames, uniformly occupied by the bees, by the coefficient 0.25 for the standard Dadant frame (435×300 mm) and by 0.2 for the standard Langstroth frame (435×230 mm).

Assessment of the Prolificity of the Queen:

The prolificity of the queen (eggs/24 hours) is determined during the visit at the end of the spring (20-31 May) by dividing the number of cells with the brood by 12 (duration of development of the brood, days), the number of eggs laid in 24 hours. The number of cells in the honeycomb is determined using the Netz frame by measuring the number of squares (5×5 cm) occupied by the brood, which is multiplied by 100, to give the total number of cells with the brood covered.

Assessment of the Degree of Infestation with *Varroa*

The assessment consists in counting the number of *Varroa* on a sample of adult bees. The value from this count is used as an index for monitoring the level of parasitism in the colony.

The method uses icing sugar and a "shaker" jar made of transparent glass with a capacity of 1 kg. The cover is a mesh made of galvanized steel of the type placed at the bottom of the hive, with a mesh size of 3 mm. The mesh allows *Varroa* mites to pass through but retains the honey bees.

The method is implemented according to the following steps: 40 to 50 g of honey bees are collected in the jar (approximately 400 bees), 100 g of icing sugar is added and the shaker jar is rolled for 1 minute so as to cover every bee in icing sugar. The icing sugar then makes it possible to separate the *Varroa* mites from the body of the host bee so that they drop off. Leave to rest for 1 minute: bees have a delousing behavior, which helps the *Varroa* mites to drop off. The icing sugar is sieved over a sieve which makes it possible to retain the *Varroa* mites and then count them. The result is given as the number of mites per 10 g of bees (approximately 100 bees) and can be expressed as a %. This rate is indicative of the *Varroa* burden in the colony. A rate between 1 and 2 indicates low *Varroa* burden. A moderate rate is between 2 and 5 and, in this case, treatment of the colonies must be scheduled. Finally, a rate greater than 5, requires emergency treatment of the colony. Our tests give a result of around 2% for worker bees.

Results

The molecules tested, their concentration in solution and their annual overall doses are listed below:

1. $(PPh_4)_2[Mo_2O_4 (EDTA)] \cdot 2.5H_2O$, abbreviated as $PPh_4$-$Mo_2O_4$-EDTA.

The feeding is carried out with 2000 g of candy containing 0.8 mg of complex then 6 to 7 L of syrup containing 0.2 mg/L of complex. The concentration of the complex in the syrup: $1.5 \times 10^{-7}$ mol/L. Overall and annual product dose: 2 mg of complex per colony 2. $Na_2[Mo_2O_4 (EDTA)] \cdot 5H_2O$, abbreviated as Na—$Mo_2O_4$-EDTA.

The feeding is carried out with 2000 g of candy containing 0.8 mg of complex then 6 to 7 L of syrup containing 0.2 mg/L of complex. The concentration of the complex in syrup: $3.0 \times 10^{-7}$ mol/L. Overall and annual product dose: 2 mg of complex per colony 3. $Li_2[Mo_2O_4 (EDTA)] \cdot 6H_2O$, abbreviated as Li—$Mo_2O_4$-EDTA.

The feeding is carried out with 2000 g of candy containing 0.8 mg of complex then 6 to 7 L of syrup containing 0.2 mg/L of complex. The concentration of the complex in syrup: $3.2 \times 10^{-7}$ mol/L; the Lithium concentration $C(Li)=6.4 \times 10^{-7}$ mol/L that is $4.5 \times 10^{-6}$ g/L. Overall and annual product dose: 2 mg of complex per colony 4. $LiCH_3COO \cdot H_2O$ as a positive control, abbreviated as Li—Ac The feeding is carried out with 2000 g of candy containing 0.8 mg of positive control product, then 6 to 7 L of syrup containing 0.2 mg/L of positive control product. The concentration of the product in syrup: $2.36 \times 10^{-6}$ mol/L that is $1.67 \times 10^{-5}$ g/L. Overall and annual product dose: 2 mg of product per colony The results are illustrated in Table 3 below.

TABLE 3

| Morpho-productive characters | Batch I, control (N* = 10) % | Batch II, PPh₄—Mo₂O₄-EDTA Overall dose 2 mg (N* = 10) % relative to batch I | Batch III, Na—Mo₂O₄-EDTA Overall dose 2 mg (N* = 10) % relative to batch I | Batch IV, Li—Mo₂O₄-EDTA Overall dose 2 mg (N* = 10) % relative to batch I | Batch V, Li—Ac Overall dose 2 mg (N* = 10) % relative to batch I |
|---|---|---|---|---|---|
| Prolificity of the queen | 100 | 107.1 | 113.3 | 111.7 | 108.8 |
| Power of the bee family | 100 | 102.1 | 101.2 | 103.3 | 98.3 |
| Quantity of honey at the first harvest | 100 | 113.3 (+13.3%) | 149.9 (+49.9%) | 143.1 (+43.1%) | 122.9 (+22.9%) |
| Degree of infestation with Varroa | 100[a] | 78.7 (−21.3%) | 86.5 (−13.5%) | 57.3 (−42.7%) | 58.4 (−41.6%) |

N* - number of hives.
[a]mean initial infestation rate of 1.78 mite/10 g of bees (approximately 100 bees) that is 1.78%.
This value is set at 100 as a reference for our tests.

We can observe that the three formula I molybdenum complexes show a significant protective effect against the infestation of bees by *Varroa destructor* relative to the untreated batch I.

At a lithium concentration almost 4 times lower, the Li—$Mo_2O_4$-EDTA complex shows a protective capacity comparable to that of the lithium acetate used as a positive control. This amount of lithium is much lower than the minimum effective amount of 2 mM used in the publication by B. Ziegelmann et al. (*Scientific Reports* 2018, 8, DOI: https://doi.org/10.1038/s41598-017-19137-5).

Moreover, two molecules of formula II tested (Na—$Mo_2O_4$-EDTA and Li—$Mo_2O_4$-EDTA) show higher effects compared to $PPh_4$-$MB_2O_4$-EDTA, both for the prolificity of the queen and the amount of honey collected.

The honeys produced in the spring and summer for batches 1 to 4 were analyzed in a COFRAC-accredited laboratory. The results of these analyses show that the honey composition is not altered by the treatment with the complexes of the invention. The honey produced comply with European standards and no trace of Mo was found in the honey, and therefore a total absence of the complexes in the honey produced.

4.2. $2^{nd}$ Test in the Hives

The $2^{nd}$ test was performed in the same apiary the following year. Feeding with the complex of the invention took place in spring. The biological tests were monitored up to the month of September.

The molecules tested, their concentration in solution and their annual overall doses are listed below:

1. $(PPh_4)_2[Mo_2O_4 (EDTA)]\cdot2.5H_2O$, abbreviated as $PPh_4$-$Mo_2O_4$-EDTA, The feeding is carried out with 2000 g of candy containing 0.8 mg of complex then 6 to 7 L of syrup containing 0.2 mg/L of complex. The concentration of the complex in syrup: $1.5\times10^{-7}$ mol/L. Overall product dose: 2 mg/colony 2. $Li_2[Mo_2O_4 (EDTA)]\cdot6H_2O$, abbreviated as Li—$Mo_2O_4$-EDTA.

The feeding is carried out with 2000 g of candy containing 0.8 mg of complex then 6 to 7 L of syrup containing 0.2 mg/L of complex. The concentration of complex in the syrup: $3.2\times10^{-7}$ mol/L; the Lithium concentration $C(Li)=6.4\times10^{-7}$ mol/L that is $4.5\times10^{-6}$ g/L; O□erall complex dose: 2 mg/colony 3. $Li_2[Mo_2O_4 (EDTA)]\cdot6H_2O$, abbreviated as Li—$Mo_2O_4$-EDTA.

The feeding is carried out with 2000 g of candy containing 2.4 mg of complex then 6 L of syrup containing 0.6 mg/L of complex. The concentration of complex in the syrup: $9.6\times10^{-7}$ mol/L; the Lithium concentration $C(Li)=1.92\times10^{-6}$ mol/L that is $1.32\times10^{-5}$ g/L. Overall complex dose: 6 mg/colony 4. $LiCH_3COO\cdot H_2O$ for comparison, abbreviated as Li—Ac The feeding is carried out with 2000 g of candy containing 0.8 mg of product then 6 to 7 L of syrup containing 0.2 mg/L of product. The concentration of product in the syrup: $2.36\times10^{-6}$ mol/L that is $1.67\times10^{-5}$ g/L. Overall product dose: 2 mg/colony The results are illustrated in Table 4 below.

TABLE 4

| Morpho-productive characters | Batch I, control (N* = 10) % | Batch II, $PPh_4$—$Mo_2O_4$-EDTA EDTA Overall dose 2 mg/hive (N* = 10) % relative to batch I | Batch III, Li—$Mo_2O_4$-EDTA Overall dose 2 mg/hive (N* = 10) % relative to batch I | Batch IV, Li—$Mo_2O_4$-EDTA Overall dose 6 mg/hive (N* = 10) % relative to batch I | Batch V, Li—Ac Overall dose 2 mg/hive (N* = 10) % relative to batch I |
|---|---|---|---|---|---|
| Power of the bee family | 100 | 120 | 120 | Not measured | 97.5 |
| Degree of infestation with Varroa | $100^a$ | 60.8 (−39.2%) | 52.6 (−47.4%) | 38.4 (−62.6%) | 69.0 (−31%) |
| Degree of larvae infestation with Varroa | $100^b$ | 56.0 (−44.0%) | 42.6 (−57.4%) | 18.4 (−81.6%) | 64.9 (−35.1%) |

N* - number of hives.

[a]mean initial infestation rate of 2.32 mite/10 g of bees (approximately 100 bees), that is 2.32%;

[b]this reference □alue of 100 corresponds to a mean initial larvae infestation rate of 28.2% measured by directly counting the infected larvae after opening one hundred cells per hive.

The results of the $2^{nd}$ test in the hives confirm the effects of the formula I complexes of the invention in protecting bees against *Varroa* infestation. Furthermore, according to the results illustrated in Table 4, this protective effect is increased when the dose is increased.

The results of the $2^{nd}$ test particularly show that the formula I complex of the invention also protects the larvae from *Varroa*. To date, there is no known treatment to protect the larvae from *Varroa*.

4.3. $3^{rd}$ Test in the Hives

A treatment campaign was carried out in the autumn-winter in apiaries located in California, near San Francisco. This region is particularly vulnerable to winter mortality of bee colonies which can reach as high as 80% in some years.

151 hives, distributed over 6 different apiaries in California to the south of San Francisco were selected. The bees were of different types: Wildflower (VSH-Italian), Beeweaver, Carniolan Californian Bee (Pope Canyon), Californian bee Tom and Italian Californian bee (Sam).

The hives were Langstroth 2 body type hives (15 frames compared to 10 for Dadant hives in Europe). Each apiary was randomly divided into two populations which served as controls and those which received the product Li—$Mo_2O_4$-EDTA (76 controls, 75 test hives).

The product Li—$Mo_2O_4$-EDTA was introduced between 25 and 28 Oct. 2019 by syringe in the form of a concentrated aqueous solution (8 g/L) in a sugar syrup into the feeding frame. 0.5 mL of this solution was introduced and dispersed in 3.5 liters of sugar syrup at 65% sugar and introduced into the hive. Each hive thus received a single overall dose of 4 mg of Li—$Mo_2O_4$-EDTA. The control hives only received sugar syrup.

The surviving colonies were counted on Jan. 7, 2020. A total of 73 colonies out of the initial 151 died, that is an overall mortality of 48.3%.

The mortality of control hives amounted to 47 colonies lost out of 76, that is 61.8% winter mortality, which is a standard result in this region.

The mortality of the test hives treated with 4 mg of Li—$Mo_2O_4$-EDTA was 26 colonies lost out of the initial 75, that is 34.7% winter mortality, which is a very significant drop in comparison to the control hives.

In conclusion, the molybdenum complex of the present invention makes it possible to significantly lower the winter mortality of bee colonies.

4.4. $4^{th}$ Test in the Hives

A second treatment campaign was carried out in the autumn-winter 2020 in apiaries located in California, near San Francisco. This region is particularly vulnerable to winter mortality of bee colonies which can reach as high as 80% in some years.

220 hives distributed over 13 different apiaries in California to the south of San Francisco were selected. Each apiary comprised between 8 and 24 hives. The bees were of different types: 165 hives of Wildflower bees (VSH-Italian) and 55 hives of Beeweaver bees (VSH-Carniolan).

The hives were Langstroth 2 body type hives (15 frames compared to 10 for Dadant hives in Europe). Each apiary was randomly divided into 4 batches of hives having a total of:

Batch 1: 55 test hives.
Batch 2: 55 hives that received Li—$Mo_2O_4$-EDTA on Sep. 20, 2020.
Batch 3: 55 hives that received Li—$Mo_2O_4$-EDTA on Oct. 12, 2020.
Batch 4: 55 hives that received Li—$Mo_2O_4$-EDTA on Sep. 20, 2020 and Oct. 12, 2020.

1 apiary only contained Wildflower type bees. 2 apiaries only contained Beeweaver type bees. The other 10 apiaries comprised Wildflower and Beeweaver bees that were evenly distributed between the 4 batches.

The product Li—$Mo_2O_4$-EDTA was introduced on Sep. 20, 2020, and/or on Oct. 12, 2020 by syringe in the form of a concentrated aqueous solution (0.8 g/L) in a sugar syrup into the frame feeder. 10 mL of this solution were introduced and dispersed in 3.5 liters of sugar syrup at 65% sugar and introduced into the hive. Each hive thus received a single overall dose of 8 mg of Li—$Mo_2O_4$-EDTA by feeding. The control hives only received sugar syrup.

The dead colonies were counted on Dec. 31, 2020. A total of 28 colonies were dead on 31 Dec. 2020, that is 12.73% of the total. The mortality rate is identical for Wildflower bees (21/165) and Beeweaver bees (7/55). The mortality per batch is distributed as follows:

Batch 1: 15 hives/55 hives, that is 27.3% losses
Batch 2: 0 hive/55 hives, that is 0% losses
Batch 3: 10 hives/55 hives, that is 18.2% losses
Batch 4: 3 hives/55 hives, that is 5.5% losses.

In conclusion, the molybdenum complex of the present invention makes it possible to significantly lower the winter mortality of the bee colonies in California at an overall dose of 8 mg per colony. Starting feeding early enough in September makes it possible to obtain significantly higher effects to feeding later.

The invention claimed is:

1. A food supplement for bees, comprising a molybdenum complex of the following formula II(i):

$$A2_m\text{-}[Mo_2O_4]\text{-}L_n \qquad \text{II(i)}$$

wherein:
A2 is a cation selected from $Li^+$ or $Na^+$,
L is a ligand selected from amino acids such as glycine (gly-), cysteine (L-$cys^{2-}$) or histidine (L-$his^-$) or poly-carboxylate ligands such as oxalate ($Ox^{2-}$), citrate ($Cit^{3-}$), ethylenediaminetetraacetate ($EDTA^{4-}$), nitrilo-triacetate ($HNTA^{2-}$), and iminodiacetate ($IDA^{2-}$),
m is the number of cations and is selected from 0, 1, 2, 3 and 4, and
n is the number of ligands and is selected from 1 and 2.

2. The food supplement for bees according to claim 1, wherein said complex is selected from the group consisting of $Na_2[Mo_2O_4(EDTA)]\cdot xH_2O$ (x=5-6), $Li_2[Mo_2O_4(EDTA)]\cdot xH_2O$ (x=3-6), $Na_2[Mo_2O_4(LCys)_2]\cdot xH_2O$.

3. The nutritional supplement for bees according to claim 1, wherein said food supplement further comprises one or several foods for bees selected from the group consisting of water, pollen, nectar, honey, sugars, vitamins, minerals, lipids, and proteins.

4. The food supplement for bees according to claim 1, wherein said food supplement is in the form of a powder, syrup, paste or an aqueous solution.

5. A method for reducing bee colony mortality, comprising feeding to a bee colony an effective amount the food supplement for bees according to claim 1.

6. The method according to claim 5, wherein the bee colony is fed the food supplement to reduce winter mortality of the bee colony.

7. A method for increasing honey production in bees, comprising feeding to a bee colony an effective amount the food supplement for bees according to claim 1.

8. The method according claim 7, wherein the bee colony is fed the food supplement to increase honey production during a first harvest.

* * * * *